United States Patent [19]
Gilchrest et al.

[11] Patent Number: 5,352,440
[45] Date of Patent: Oct. 4, 1994

[54] METHODS FOR INCREASING MELANIN CONTENT IN MELANOCYTES USING DIACYLGLYCEROLS AND USES THEREOF

[75] Inventors: Barbara A. Gilchrest, Brookline, Mass.; Philip R. Gordon, Philadelphia, Pa.

[73] Assignee: Trustees of Boston University, Boston, Mass.

[21] Appl. No.: 934,872

[22] Filed: Aug. 21, 1992

Related U.S. Application Data

[63] Continuation-in-part of Ser. No. 635,405, Dec. 11, 1990, abandoned, Ser. No. 625,236, Dec. 10, 1990, abandoned, and Ser. No. 624,453, Dec. 10, 1990, abandoned, which is a continuation of Ser. No. 175,129, Mar. 30, 1988, abandoned.

[51] Int. Cl.$^5$ .................. A61K 7/18; A61K 31/22; A61K 31/225
[52] U.S. Cl. .................. 424/59; 514/546; 514/542; 514/549
[58] Field of Search .................. 514/546, 547, 549; 424/59

[56] References Cited

U.S. PATENT DOCUMENTS

| | | | |
|---|---|---|---|
| 4,443,546 | 4/1984 | Stemerman et al. | 435/240 |
| 4,508,706 | 4/1985 | Pawelek et al. | 424/60 |
| 4,618,484 | 10/1986 | Pawelek | 424/1.1 |
| 4,695,449 | 9/1987 | Pawelek | 424/1.1 |
| 4,816,450 | 3/1989 | Bell | 514/25 |

FOREIGN PATENT DOCUMENTS

| | | |
|---|---|---|
| 0255964 | 2/1988 | European Pat. Off. |
| WO91/07167 | 5/1991 | PCT Int'l Appl. |
| WO91/07168 | 5/1991 | PCT Int'l Appl. |

OTHER PUBLICATIONS

Molleyres, L. P. and Rando, R. R., "Structural Studies on the Diglyceride-mediated Activation of Protein Kinase C", *J. Biol. Chem.* 263(29):14832–14838 (1988).
Ganong, B. R. et al., "Specificity and Mechanism of Protein Kinase C Activation by sn-1,2-Diacylglycerols", *Proc. Natl. Acad. Sci. USA* 83:1184–1188 (1986).
Mori, T. et al. "Specificity of the Fatty Acyl Moieties of Diacylglycerol for the Activation of Calcium-Activated, Phospholipid-Dependent Protein Kinase", *J. Biochem.* 91:427–431 (1982).
Sasakawa, N., et al., "Induction of Ornithine Decarboxylase Activity by 1-Oleoyl-2-Acetyl-Glycerol in Isolated Mouse . . . ", *Diochemical & Biophys. Res. Comms.* 128(2): 913–920 (1985).
Smart, R. C., et al., "sn-1,2-Diacylglycerols mimic the effects of 12-0-tetradecanoylphorbol-13-acetate . . . ", *Carcinogenesis*, 7(11): 1865–1870 (1986).
Wren, F., et al., "Ultraviolet-Mediated Melanogenesis in Cultured Human Melanocytes is not Modulated by Prostaglandins el, E2 or TPA", Abstr. 29: vol, 91(4) (1988).
Gordon, P. R., et al., "Human Melanogenesis is Stimulated by Diacylglycerol", *Jour. Of Invest. Derm.*, 93 (5): 700–702 (1989).
Korner, A., et al., "Activation of melanoma tyrosinase by a cyclic AMP-dependent protein kinase in a cell–free system", *Nature*, 267:444–447 (1977).
Nishizuka, Y., "Studies and Perspectives of Protein Kinase C", *Science*, 233: 305–312 (1986).
Friedmann, P. S., et al., "Ultraviolet Radiation Directly Induces Pigment Production by Cultured Human Melanocytes", Journ. of Cell. Phys., 133:88–94 (1987).
Friedmann, P. S., et al., "Ultraviolet Stimulated Melanogenesis by Human Melanocytes is Augmented by Di–Acyl Glycerol but not TPA" Journ. of Cell. Phys. 142:334–341 (1990).

(List continued on next page.)

Primary Examiner—Gregory Hook
Attorney, Agent, or Firm—Hamilton, Brook, Smith & Reynolds

[57] ABSTRACT

A method for inducing melanin synthesis in melanocytes, thereby increasing the melanin content of melanocytes and, thus, increasing pigmentation, melanocytes with increased melanin content produced by these methods, and uses thereof.

6 Claims, 6 Drawing Sheets

OTHER PUBLICATIONS

Gordon, P. R., et al., "Relative Responsiveness of Cultured Human Epidermal Melanocytes and Melanoma Cells to Selected Mitogens", Jour. of Invest. Derm., 87(6):723–727 (1986).

Ganong, B. R., et al., "Synthesis of Cell–Permeant Diacylglycerol Analogs for Structure–Function Analysis of Protein Kinase C and Other Enzymes" Meth. of Enzym. 141:313–320 (1987).

Stralfors, P., "Insulin stimulation of glucose uptake can be mediated by diacylglycerol in adipocytes", Nature, 335:554–556 (1988).

Bolognia, J. L., "Hairless Pigmented Guinea Pigs: A New Model for the Study of Mammalian Pigmentation", Pigment Cell Res. 3:150–156 (1990).

Imokawa, G., et al., "Differential Analysis of Experimental Hyper-Melanosis Induced by UVB, PUVA, and Allergic Contact Dermatitis Using a Brownish Guinea Pig Model", Arch. Dermatol. Res. 278:352–362 (1986).

Gilchrest, B. A., et al., "Selective Cultivation of Human Melanocytes from Newborn and Adult Epidermis", Jour. of Invest. Dermat. 83:370–376.

Castagna, M., "Phorbol esters as signal transducers and tumor promoters", Biol of the Cell, 49:3–14 (1987).

Nordlund, J. J., et al., "Prostaglandin E2 and D2 but Not MSH Stimulate the Proliferation of Pigment Cells in the Pinnal Epidermis of the DBA/2 Mouse", Jour. of Invest. Dermat., 86(4): 433–437 (1986).

Lerner, A. B., et al., "Transplantation of Human Melanocytes", Jour. of Invest. Dermat., 89(3): 219–224 (1987).

Halaban, R., et al., "Tyrosinase activity and abundance in Cloudman Melanoma Cells", Arch. of Biochem. and Biophys., 230(1): 383–387 1984.

Abdel, Z. A., et al., "Long –term & Residual Melanotropin–Stimuated Tyrosinase Activity In S91 Melanoma Cells is Density Dependent", in Vitro Cell. & Dev. Biol. 22(2): 75–81 (1986).

Gordon, P. R., et al., "Regulation of Human Melanocyte Growth, Dendricity, & Melanization by Keratinocyte Derived Factors", Jour. of Invest. Dermat. 92(4):565–572 (1989).

Gordon, P. R., et al., "Cultured Keratinocytes Release Factors that Increase Melanocyte Growth, Melanization and Dendricity", Abstr. Clinical Research 36(3):1988.

Pittelkow, M. R., et al., "Serum–Free Culture of Normal Human Melanocytes: Growth Kinetics and Growth Factor Requirement", Jour. of Cell. Phys. 140:565–576 (1989).

Gordon, P. R., et al., "Cultured Keratinocytes Release Factors that increase Melanocyte Growth, Melanization and Dandricity", J. Invest. Dermatol., 90: 564 (Abstract (1988).

Gilchrest, B. A., et al., "A culture system for the study of human melanocyte physiology", Structure and Function of Melanin, K., Jimbow (ed.) Vol. 4 (Proceedings of teh XIII Intl. Pigment Cell Conf.) Fuji–shoin Co. Ltd., Sapporo, Japan, pp. 1–13 (1987).

Nordlund, J. J., et al., "Mechanisms for Post–Inflammatory Hyperpigmentation and Hypopigmentation", Advances in Pigment Cell Res. pp. 219–236 (1988).

Rosen, Cheryl, F., et al., "A Comparison of the Melanocyte Response to Narrow Band UVA and UVB exposure In Vivo", Journ. of Invest. Dermatol. 88:(6): 774–781 (1987).

Hadley, M. E., et al., "Biological actions of melanocyte–stimulating hormone", Ciba Foundation Symposium 81 pp. 244–262 (1981).

Kitajima, Y., et al., "Biphasic Effects of 12–0–Tetradecanoylphorbol–13 acetate on the cell morphology of low calcium–grown human epidermal carcinoma cells": Involvement of Translocation and Down Regulation of protein Kinase C[1], Cancer Res. 48: 964–970 (1988).

METHODS FOR INCREASING MELANIN CONTENT IN MELANOCYTES USING DIACYLGLYCEROLS AND USES THEREOF

GOVERNMENT SUPPORT

The invention described herein was supported in whole, or in part, by grants from the U.S.D.A. (Contract No. 533K-06-5-10) and the National Institutes of Health (Grant No. CA 45687).

RELATED APPLICATIONS

This application is a continuation-in-part of Ser. No. 07/624,453 filed Dec. 10, 1990, now abandoned, which is a continuation of Ser. No. 07/175,129, filed Mar. 30, 1988, now abandoned, and of Ser. No. 07/625,236, filed Dec. 10, 1990, now abandoned, and Ser. No. 07/625,405, filed Dec. 11, 1990, now abandoned. The teachings of these three related applications are incorporated herein by reference.

BACKGROUND OF THE INVENTION

Melanins are a class of structurally related compounds that serve as the principal pigment (color) of vertebrate skin, hair, fur and feathers. Melanin pigmentation is largely responsible for normal skin and hair color, and provides protection against ultraviolet light damage from sunlight and other light sources. Melanins are synthesized exclusively by specialized cells termed "melanocytes" found in the skin and hair follicles. Once synthesized, melanin is transferred via the cellular dendrites (extensions) of the melanocyte to the surrounding keratinocytes, the most abundant cell type in the epidermis. The rate of melanin synthesis, and the subsequent transfer of melanin by melanocytes via their dendrites, appear to be influenced by ultraviolet light exposure.

Darker skin pigmentation is considered desirable by many persons, socially and aesthetically. At present, the most common means of darkening skin is sun-tanning, using either natural sunlight or specially designed ultraviolet light sources (tanning lamps).

However, extended exposure of human skin to ultraviolet light is well known to have adverse long and short term health consequences, specifically skin cancer and photoaging (long term) and the risk of painful sunburn and keratitis (short term). Furthermore, light-skinned individuals are highly susceptible to sun-induced skin cancers, face a higher risk of melanoma (skin cancer), and incur photoaging or dermatoheliosis, a condition characterized by wrinkling, irregular pigmentation, and surface roughness. However, even darker skinned individuals exposed to prolonged sunlight incur a high risk of skin cancer and exacerbated aging.

Some individuals are unable to achieve even normal pigmentation due to abnormal conditions such as vitiligo, piebaldism, albinism, and other hypopigmentation disorders, or as the result of certain inflammatory processes. The result of such abnormal conditions, in the extreme, is total depigmentation of both hair and skin. In less severe instances, some hypopigmentation disorders result in patchy white areas within the skin and hair. All of these conditions can cause severe cosmetic and psychological problems.

Melanocytes and melanin content are also responsible for the pigmentation of hair, fur and feathers. For example, graying of hair is due to a decrease in number or activity of the melanocytes residing in the hair bulb. In nonhuman instances, changes in melanocyte content and melanin synthesis rate result in changes in the color of pelage, fur, wool, and other kinds of animal hair.

The ability to increase melanin synthesis, and thus increase the melanin content of melanocytes, would provide an alternate method of darkening skin pigmentation without the hazards of ultraviolet irradiation. Moreover, increasing the melanin content of hair would provide a method for darkening graying hair. Furthermore, the ability to maintain melanin production would minimize discoloration in fur, wool, feathers, and other animal hair counterparts and would permit production of biologically engineered fur, wool., and feathers with desired levels of pigmentation.

SUMMARY OF THE INVENTION

The present invention relates to a method for inducing melanin synthesis in melanocytes, thereby increasing the melanin content of melanocytes and, thus, increasing pigmentation. In the present method, a diacylglycerol which induces melanin synthesis in melanocytes is contacted with melanocytes, thereby inducing melanin synthesis in the melanocytes and increasing the melanin content of the melanocytes. The increased melanin content in melanocytes results in increased pigmentation, or darkened color, of the melanocytes. The melanocytes that are contacted with the diacylglycerol may be present in vertebrate skin, hair, fur, or feathers.

The term diacylglycerol, or DAG, as used herein, includes the naturally-occurring 1,2-diacylglycerol, and synthetic DAG analogues and derivatives. DAGs are able to induce melanin synthesis and thus, produce an increase in melanin content in melanocytes without altering melanocyte proliferation. Moreover, DAGs do not increase dendricity of melanocytes. DAGs are therefore selective in their biological action and cellular function and are generally limited to being able to induce melanin synthesis and production specifically within preexisting melanocytes. Particularly useful in the present method is a water dispersible analogue of DAG, 1-oleoyl-2-acetylglycerol, or OAG.

DAGs can be used to treat a variety of conditions resulting from decreased production of, or complete absence of, melanin in melanocytes. Such conditions include vertiligo, tinea versicolor, albinism and other hypopigmentation conditions. DAGs can also be used cosmetically to tan the skin and darken hair color, as well as prevent discoloration of animal fur, wool, feathers and other animal hair counterparts.

In a preferred embodiment, a DAG which induces melanin synthesis, or a combination of such DAGs, can be combined in admixture with a biologically compatible fluid carrier to form a topical formulation which can be applied to, or contacted with, melanocytes in skin and increase the melanin content of skin in vivo, thus increasing the pigmentation of the skin. This embodiment is particularly useful as a method for cosmetic tanning of the skin of a human.

In another embodiment, DAGs may be employed with conventionally known media and culture techniques for in-vitro culture of melanocytes with increased melanin content. In each instance, the use of DAGs will increase melanin synthesis within melanocytes, thus increasing the melanin content of the melanocytes and, consequently, increase pigmentation.

The present invention also relates to melanocytes with increased melanin content produced by the methods disclosed herein. Melanocytes with increased melanin content can be useful in preparing skin grafts for implantation into acquired, or congenital, white patches of skin so that the skin can attain normal, and even, coloration.

BRIEF DESCRIPTION OF THE FIGURES

The present invention may be more easily and completely understood when taken in conjunction with the accompanying drawings.

DETAILED DESCRIPTION

Figure 1A:
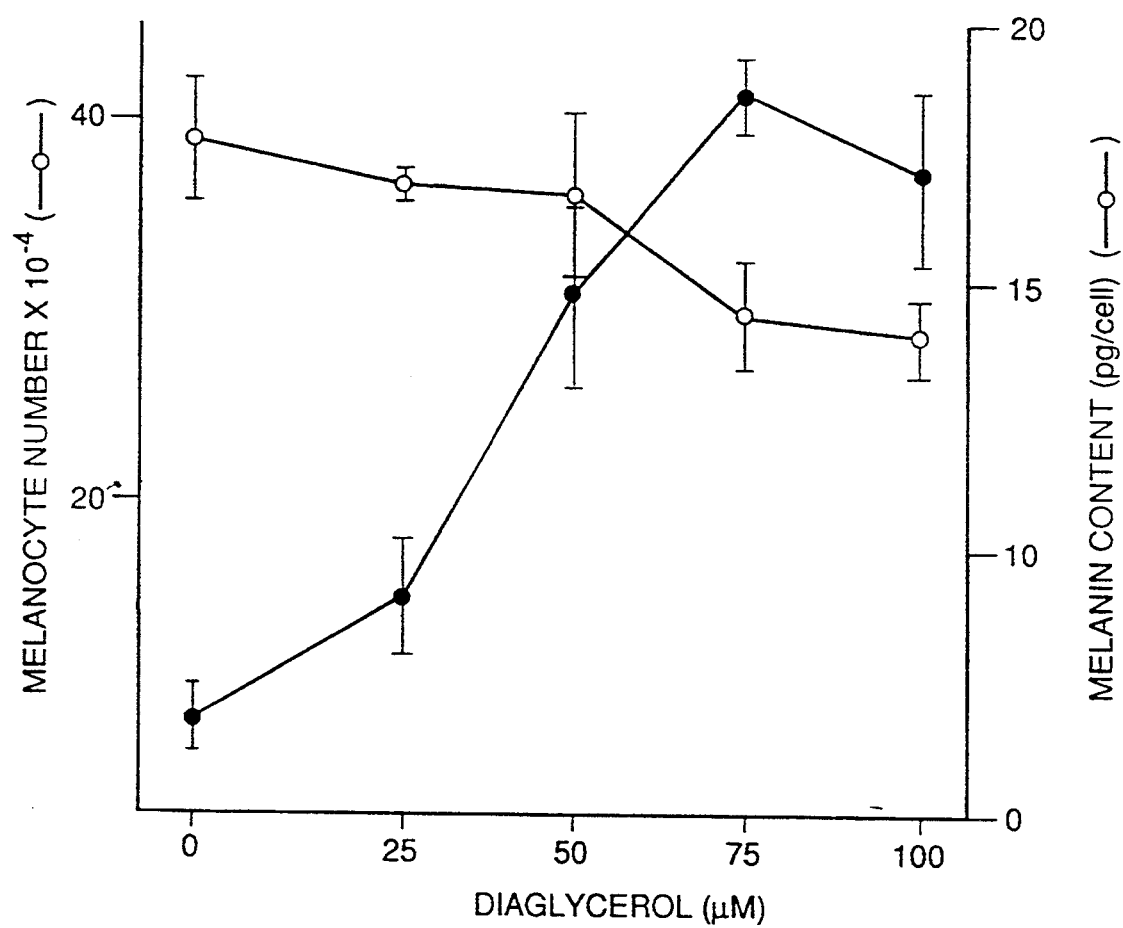
FIGS. 1a and 1b are graphs illustrating the effects of a diacylglycerol upon human melanocyte proliferation and melanin content.

The present invention relates to a method for inducing melanin synthesis in melanocytes, thereby increasing the melanin content of melanocytes and, thus, increasing pigmentation. The term pigmentation as used herein, means the deposit of melanin, or pigment, in the skin, hair, fur and feathers of vertebrates.

Specifically, the method for inducing melanin synthesis and, thus, increasing the melanin content in melanocytes, relates to the use of a class of chemical compounds called diacylglycerols, or DAGs, including naturally-occurring DAG, synthetic analogues of DAG and derivatives of DAG.

Although, the exact mechanism of melanin synthesis is unknown, considerable evidence implicates the cyclic 3', 5'-adenosine monophosphate (cAMP)-mediated intracellular signal transduction pathway in murine melanogenesis. (Korner, A. and Pawelek, J. M., *Nature* 267:44 (1977); Halaban, R., et al. *J. Cell. Biol.* 97:480 (1983)). However, it has not been possible to establish a firm role for cAMP in human melanogenesis. (Friedmann, P. S. and Gilchrest, B. A., *J. Cell. Physiol.* 133:88 (1987)).

Another major second messenger for intracellular signal transduction is diacylglycerol, or DAG. Specific stimuli activate phospholipase C, releasing DAG from cell membranes, which, in turn, activates protein kinase C (PKC). (Nishizuka, Y., *Science* 233:305 (1986)). As presented herein, it has been now demonstrated that DAG is a biologically active and potent stimulant of melanin synthesis, and that melanin content of melanocytes is increased as a result of contact with DAG.

Chemical Structure And Occurrence of Diacylglycerol

Naturally-occurring diacylglycerols play a prominent role in intracellular signal transduction pathways as physiological activators of protein kinase C (PKC). (Berridge, N. J., *Ann. Rev. Biochem.* 56:159193 (1987); Nishizuka, Y., *Science* 233:305-312 (1986)). Recently, synthetic DAG analogues have been prepared that also have biological activity as activators of PKC. (Ganong, B. R. and Bell, R. M., *Meth. Enzymol.* 141:313-320 (1987)). As used herein, the term DAG includes naturally-occurring diacylglycerols, as well as synthetic analogues and derivatives of naturally-occurring diacylglycerols.

DAG analogues can be prepared by conventional methods and have general chemical structures of Compounds A, B, and C, as follows:

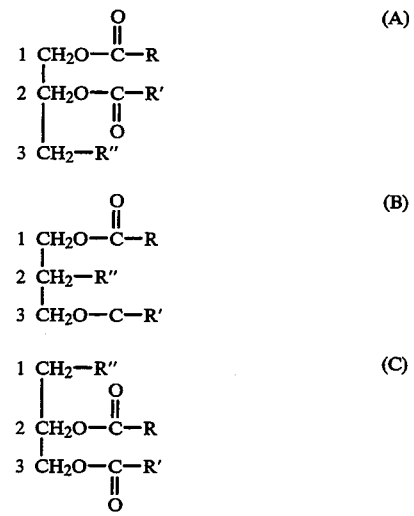

in which R and R' are carbon containing moieties. R and R' are usually long-chain (more than 14 carbon atoms) carboxylic acids and may contain one or more carbon-carbon double bonds. In most instances, R and R' are chemically different in composition. (Ganong, B. R. and Bell, R. M., *Meth. Enzymol.* 141:313-320 (1987)).

In comparison, R" can be any chemical entity which does not form a carbon ester linkage with the adjoining carbon atom in the glycerol structure. Accordingly, R" may include a hydroxyl group, a phosphate group, a sulfur atom, an ether group, a halide, a nitrogen containing entity, or a hydrogen. (Ganong, B. R. and Bell, R. M., *Meth. Enzymol.* 141:313-320 (1987)).

Diacylglycerols Useful in the Present Method

Diacylglycerols (DAGs) useful in the present method are those DAGs, naturally-occurring, as well as synthetic analogues, which are biologically active (i.e., induce melanin synthesis) and thus, increase melanin content in melanocytes under in vivo and/or in-vitro conditions. The naturally occurring DAGs are derivatives of phosphatidylinositol and usually contain a long-chain mono-unsaturated fatty acid acylated to the number one carbon position in the glycerol structure. Also, DAGs typically contain a highly unsaturated fatty acid, primarily arachidonic acid, acylated to the number two carbon position in the glycerol structure.

A preferred DAG in the present method is 1-oleoyl-2-acetyl-glycerol, or OAG, a synthetic DAG analogue. OAG is particularly useful because of its solubility in water and its ability to produce a dose-dependent response in melanin content with no concomitant effect upon proliferation and/or growth of melanocytes. Additionally, other preferred DAGs contain a free hydroxyl group at the number three carbon position in the glycerol structure and have a three carbon backbone structure similar to glycerol.

DAGs believed to be biologically active and potent for stimulation of melanin synthesis within melanocytes include, but are not limited to:

Diacylglycerol Analogues 1,2-diformylglycerol
1,2-diacetylglycerol
1,2-dibutanoylglycerol
1,2-dihexanoylglycerol
1,2-dioctanoylglycerol
1,2-didecanoylglycerol
1,2-didodecanoylglycerol
1,2-diteradecanoylglycerol
1,2-dihexadecoylglycerol
1,2-dioctadecanoylglycerol
1,2-dieicosanoylglycerol
1,2-didocosanoylglycerol
1,2-ditetracosanoylglycerol
1,2-dipalmitoylglycerol
1,2-dioleoylglycerol
1,2-dilinoleoylglycerol
1,2-dilinolenoylglycerol
1,2-arachidonoylglycerol
1-octanoyl-2-formyl-glycerol
1-octanoyl-2-acetyl-glycerol
1-octanoyl-2-butanoyl-glycerol
1-octanoyl-2-hexanoyl-glycerol
1-octanoyl-2-decanoyl-glycerol
1-octanoyl-2-dodecanoyl-glycerol
1-octanoyl-2-tetradecanoyl-glycerol
1-octanoyl-2-hexadecanoyl-glycerol
1-octanoyl-2-octadecanoyl-glycerol
1-octanoyl-2-eicosanoyl-glycerol
1-octanoyl-2-docosanoyl-glycerol
1-octanoyl-2-tetracosanoyl-glycerol
1-octanoyl-2-palmitoyl-glycerol
1-octanoyl-2-oleoyl-glycerol
1-palmitoyl-2-formyl-glycerol
1-palmitoyl-2-acetyl-glycerol
1-palmitoyl-2-butanoyl-glycerol
1-palmitoyl-2-hexanoyl-glycerol
1-palmitoyl-2-octanoyl-glycerol
1-palmitoyl-2-decanoyl-glycerol
1-palmitoyl-2-dodecanoyl-glycerol
1-palmitoyl-2-tetradecanoyl-glycerol
1-palmitoyl-2-hexadecanoyl-glycerol
1-palmitoyl-2-octadecanoyl-glycerol
1-palmitoyl-2-eicosanoyl-glycerol
1-palmitoyl-2-dodcosanoyl-glycerol
1-palmitoyl-2-oleoyl-glycerol
1-palmitoyl-2-linoleoyl-glycerol
1-palmitoyl-2-arachidonoyl-glycerol
1-oleoyl-2-formyl-glycerol
1-oleoyl-2-acetyl-glycerol
1-oleoyl-2-butanoyl-glycerol
1-oleoyl-2-hexanoyl-glycerol
1-oleoyl-2-octanoyl-glycerol
1-oleoyl-2-decanoyl-glycerol
1-oleoyl-2-dodecanoyl-glycerol
1-oleoyl-2-tetradecanoyl-glycerol
1-oleoyl-2-palmitoyl-glycerol
1-oleoyl-2-linoleoyl-glycerol
1-oleoyl-2-arachidonoyl-glycerol
1-hexanoyl-2-formyl-glycerol
1-hexanoyl-2-acetyl-glycerol
1-hexanoyl-2-butanoyl-glycerol
1-hexanoyl-2-octanoyl-glycerol
1-hexanoyl-2-decanoyl-glycerol
1-hexanoyl-2-dodecanoyl-glycerol
1-hexanoyl-2-tetradecanoyl-glycerol
1-hexanoyl-2-hexadecanoyl-glycerol
1-hexanoyl-2-octandecanoyl-glycerol
1-hexanoyl-2-eicosanoyl-glycerol
1-hexanoyl-2-palmitoyl-glycerol
1-hexanoyl-2-oleoyl-glycerol
1-hexanoyl-2-linoleoyl-glycerol
1-hexanoyl-2-arachidonoyl-glycerol

Effects Of Diacylglycerols on Human Melanocytes

The following experiments investigate the biological effects of DAG upon human melanocytes and reveals the effects of pretreatment of human melanocytes with specific agents prior to incubation with a DAG.

A first set of experiments was performed which used human melanocytes cultured as described in Example 1. Human melanocytes were combined with 1-oleoyl-2-acetyl-glycerol (OAG) in complete melanocyte medium and incubated together for a period of 6 days at 37° C. Melanin content of the cells was determined as described in Example 2. The results are graphically illustrated by FIGS. 1a and 1b, which show a dose dependent response of increased melanin content at concentration levels ranging from 25-200 uM OAG, with no significant effect on melanocyte proliferation or growth.

At a concentration of 100 uM, OAG produced an average of a 4-fold increase in melanocyte melanin content per cell over the untreated control (i.e., melanocytes cultured as in Example 1, combined with complete melanocyte medium and incubated as were treated cells). Importantly, OAG did not increase the dendricity of human melanocytes and did not significantly affect human melanocyte growth.

A second set of experiments was conducted in which the cultured human melanocytes were first pretreated with tetradecanoyl phorbol-13-acetate (TPA), a known activator of protein kinase C. It is known that TPA first stimulates and subsequently, profoundly suppresses PKC activity for a prolonged period.

Initially, the human melanocytes were obtained and grown as previously described in Example 1. Subsequently, the cultured human melanocytes were combined with 100 nM of TPA in melanocyte medium and incubated at 37° C. for 24 hours. OAG was then added and the culture incubated again for 6 days. The melanin content of the cells was then evaluated according to Example 2. The results are graphically illustrated by FIGS. 2 and 3 respectively.

Figure 2:
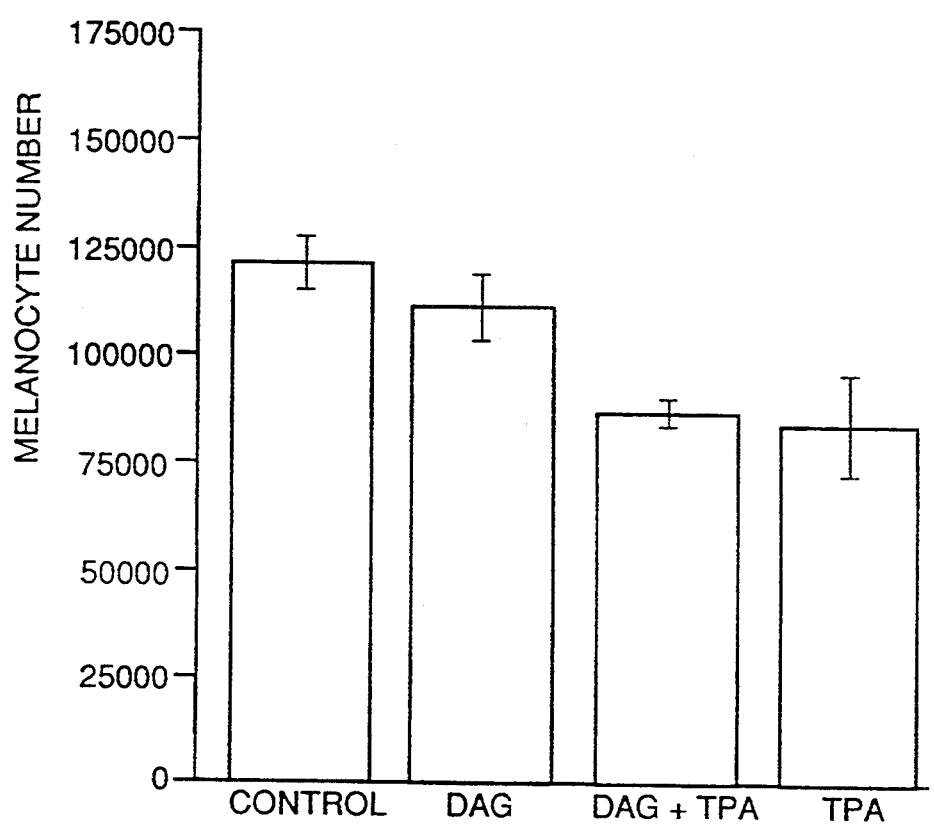
FIG. 2 is a graph illustrating the effects of a diacylglycerol upon the proliferation of human melanocytes when administered alone and after pretreatment with a phorbol ester.
Figure 3:
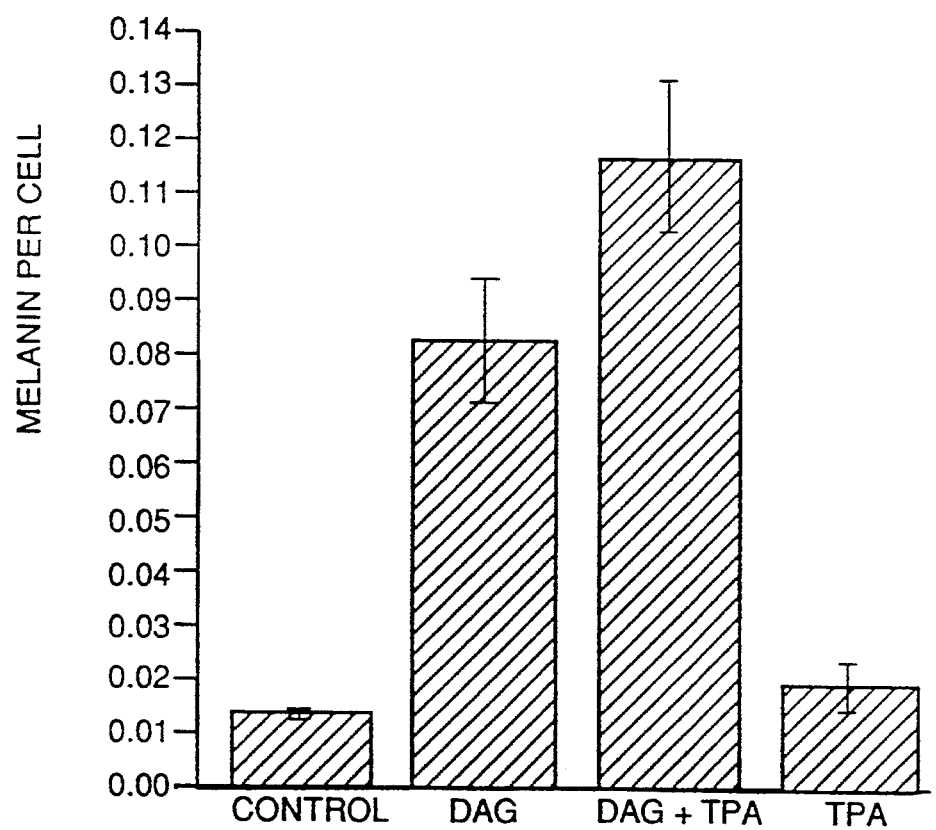
FIG. 3 is a graph illustrating the effects of a diacylglycerol upon melanin production with human melanocytes when administered alone and after pretreatment with a phorbol ester.

FIG. 2 demonstrates that neither OAG, nor the pretreatment with TPA, or their combination, has any substantial affect on human melanocyte proliferation. However, in comparison, FIG. 3 demonstrates significant increases in melanin content per human melanocyte as a function of TPA pretreatment in combination with OAG treatment. Thus, pre-exposure to TPA actually enhanced the OAG effect on melanin synthesis.

Consequently, for maximum melanin production, it may be desirable to pretreat human melanocytes prior to contact with the chosen DAG.

Effects Of Diacylglycerols On Non-Human Melanocytes

This set of experiments was performed to evaluate the effect of DAG on melanocytes derived from non-human sources, rather than humans. In these experiments, murine S91 melanoma cells were grown and maintained in culture using conventional techniques (Friedmann, P. S. and Gilchrest, B. A., *J. Cell. Physiol.* 133:88–94 (1987)). The S91 melanoma cells were then combined with 100 uM of OAG, or with 100 uM of 3-isobutyl-1-methylxanthine (IBMX), which increases cAMP levels and also induces melanin synthesis in S91 melanoma cells. Each chemical agent was combined with the S91 melanoma cells in Dulbecco's Minimal Eagle's Medium containing 2% FBS and incubated at 37° C. for 7 days. The results are graphically illustrated by FIGS. 4 and 5, respectively.

Figure 4:
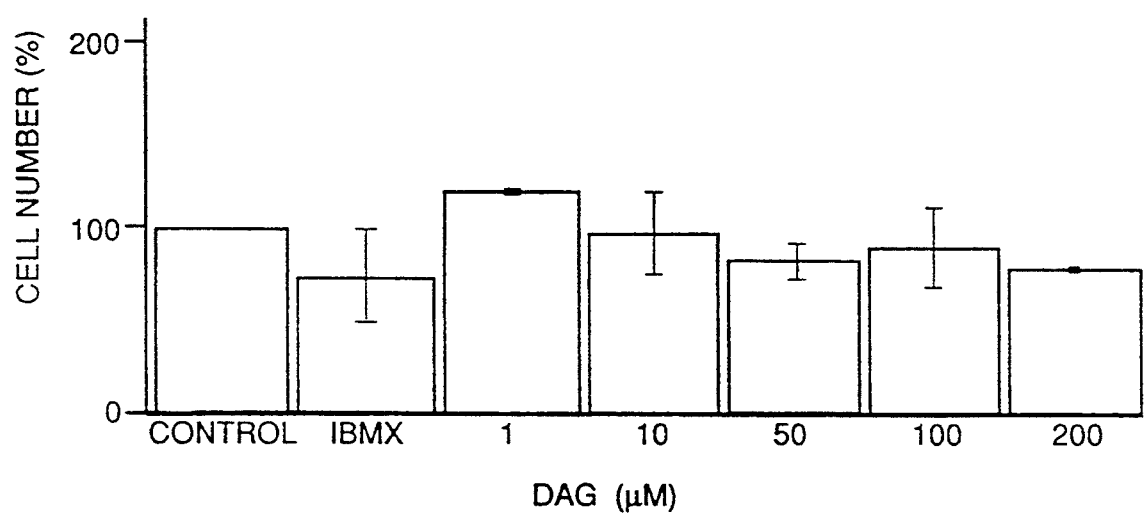
FIG. 4 is a graph illustrating the effects of a diacylglycerol on the proliferation of S91 murine melanoma cells in culture.
Figure 5:
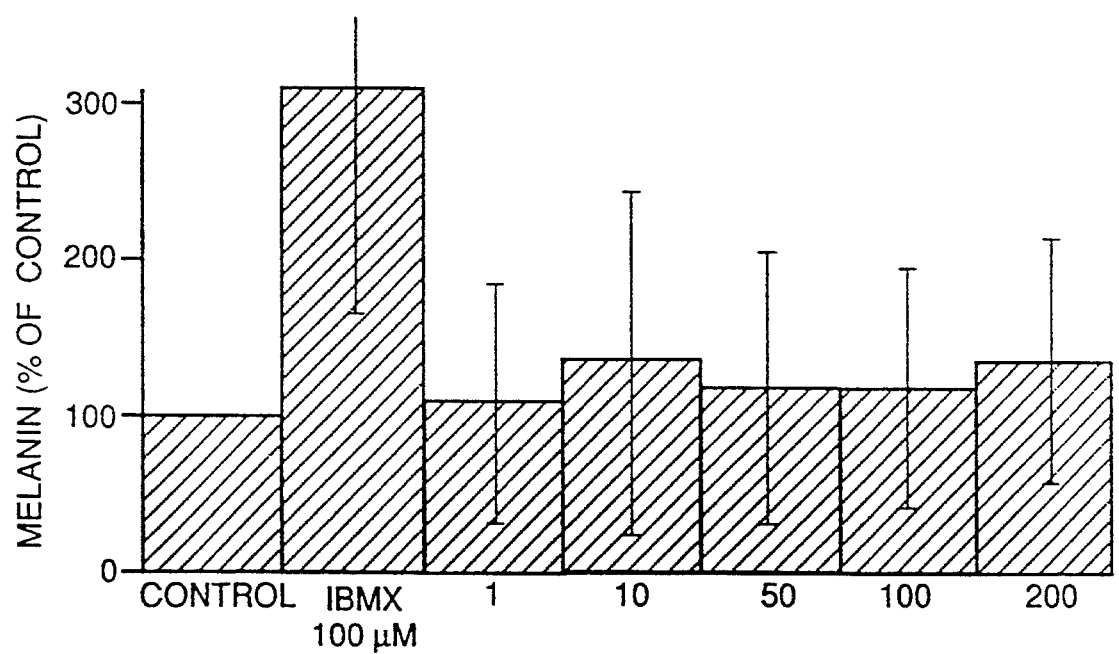
FIG. 5 is a graph illustrating the effects of a diacylglycerol upon the melanin content of S91 murine melanoma cells in culture.

FIG. 4 demonstrates that OAG at concentrations ranging from 1–200 uM failed to induce proliferation of S91 melanoma cells. IBMX was similar in effect and also failed to produce any cellular growth. In comparison, FIG. 5 reveals major differences between the ability of OAG and IBMX to induce an increase in melanin production. Clearly, IBMX at a concentration of 100 uM caused a major increase in melanin production in S91 melanoma cells. In comparison, OAG under the experimental conditions indicated, failed to induce any substantial increase in melanin production in comparison to controls.

These results suggest that the biological effects of DAG are selective and discriminatory in accordance with the source of origin of the melanocytes. Specifically, under the conditions used, OAG has no meaningful effect on S91 murine melanoma cells. On the other hand, contact of OAG to human melanocytes results in substantial increases in melanin content without concomitant cell proliferation of the human melanocytes.

In Vivo Effects of Diacylglycerols

Experiments were also conducted in adult guinea pigs to evaluate the effects of DAGs in vivo. Guinea pigs are accepted models for studies of the human pigmentary system because they contain melanin in the epidermis, as well as in hair follicles, which is similar to the distribution of melanin in human skin. (Bolognia, J. L., et al., *Pigment Cell Res.* 3:150 (1990); Imokawa, G., *Arch. Dermatol. Res.* 278:352 (1986)).

As described in detail in Example 3, increased pigmentation of guinea pig skin in OAG-treated areas was observed at 4–5 days, and persisted for approximately one month, fading gradually afterwards. At all time points, the OAG-treated areas were darker in color than the control areas (i.e., vehicle-alone-treated areas).

In addition, punch biopsies of OAG-treated, vehicle-treated, and adjacent untreated skin were obtained 7 days after the last application (14 days after the first application). Also as described in Example 3, the biopsies were processed and stained with Fontana Mason stain which contains a reducing agent known to stain melanin a black color to confirm that the pigment was melanin. The histological presence of pigmentation in the skin specimens is greatest in the OAG-treated skin, and least in the untreated adjacent skin tissue. In all specimens, the pigmentation is concentrated in the lower epidermis, exactly as seen in normal skin at baseline and after tanning induced by sun exposure.

These experiment clearly demonstrate the ability of OAG to increase epidermal pigmentation in-vivo in a manner clinically and histologically identical to normal sun-induced tanning. Thus, these data establish the ability of a DAG to induce melanogenesis in melanocytes, in-vivo.

Diacylglycerol Administration And Manner Of Use

DAGs, specifically OAG, are able to produce increases in melanocyte melanin content, when contacted with melanocytes, without altering melanocyte proliferation.

DAGs may be employed in the method of the present invention as follows: in a method for pigmenting (coloring) skin grafts, allografts, and autografts in-vitro and in-vivo; for treating hypopigmentation disorders such as vitiligo, albinism, piebaldism, and post-inflammatory hypopigmentation; as a sun-light independent human skin tanning agent; as a tanning accelerator in the presence of natural sunlight; as a treatment for darkening, or repigmenting, hair in-vivo; for preventing gray (depigmented) hair in-vivo; and for darkly colored pelage, fur, and wool in-vivo by animals.

DAGs are particularly useful to induce melanin synthesis in humans to tan the skin in the absence of sunlight; to accelerate skin tanning in the presence of natural sunlight; and to provide a treatment to darken gray (depigmented) hair.

It is intended that the DAGs of the present method be employed both in-vivo and in-vitro. For in-vivo use, it is desirable that contact with melanocytes be accomplished by topical administration of one or more DAGs directly to the skin or hair of an individual. For this purpose, the DAGs are intended to be admixed in a pharmacological topical carrier such as a gel, an ointment, a lotion, or a cream and will include such carriers as water, glycerol, alcohol, propylene glycol, fatty alcohols, triglycerides, fatty acid esters, or mineral oils.

Other possible topical carriers are liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers, and similar agents may be added as necessary.

In addition, in certain instances, it is expected that the DAGs described herein may be disposed within devices placed upon, in, or under the skin; such devices include patches, implants, and injections which release the DAG into the skin either by passive or active release mechanisms.

For in-vivo use, it is preferred that the DAG analogue be present in a final concentration range from 0.10–20.0 mM in a fluid carrier material. However, the actual preferred amounts of DAG to be administered will vary according to the specific compound being utilized, the particular compositions formulated, the mode of application, and the particular site of the individual being treated. The concentration of DAG effective to increase melanin synthesis and thus, increase melanin content of melanocytes can be determined using known, conventional pharmacological protocols and evaluated using the cell culture and animal model described herein.

Alternatively, for in-vitro use as a laboratory reagent with cultures of melanocytes, the DAG may be added directly to the culture media surrounding the living cells at a concentration sufficient to induce melanin synthesis, and thus increase melanin content in the cultured melanocytes. Determinations of inhibitory and toxic concentrations for the DAG can also be made using known methods and evaluated using techniques described herein, and other methods known to those skilled in the art.

The invention is further illustrated by the following examples, which are not intended to be limiting in any way.

EXAMPLE 1

Melanocyte Cell Culture

Neonatal foreskins obtained within two hours of elective circumcision were the source of human keratinocytes and melanocytes. The epidermis was separated from the dermis after overnight incubation in 0.25% trypsin. Melanocytes were established in primary culture from epidermis prepared according to the procedure of Gilchrest et al. (*J. Invest. Dermatol.* 83:370–376 (1984)).

In brief, operative specimens were cut into fragments, rinsed in calcium-free phosphate-buffered saline (PBS); and incubated in 0.25% trypsin (GIBCO) overnight at 4° C. The epidermal portions of the fragments were separated from the dermis with forceps; incubated for 10 minutes in 0.02% EDTA at 37° C.; vortexed to yield a single cell suspension; inoculated at a concentration of $10^6$ cells per 35 -mm dish in melanocyte growth medium; and maintained at 37° C. in 8% carbon dioxide and 92% air. Cultures were provided with fresh melanocyte growth medium three times weekly.

Melanocyte growth medium is a serum-free medium, Medium 199 (GIBCO 400-1100), supplemented with 10 ng/ml epidermal growth factor, 10 nM triiodothyrine, 10 ug/ml transferrin, 10 ug/ml insulin, 1 nM cholera toxin and 100 ug/ml bovine hypothalamic extract.

EXAMPLE 2

Melanocyte Bioassay

Melanocytes were seeded at $2 \times 10^4$ cells per 35 mm dish and combined with DMEM supplemented with 10 ug/ml insulin, $10^{-9}$M triiodothyrine, 10 ug/ml transferrin, $1.4 \times 10^{-6}$M hydrocortisone, 10 ng/ml epidermal growth factor, $10^{-9}$M choleragen, 2% FBS and 100 ug/ml of BHE, now designated as complete melanocyte medium. After 24 hours incubation at 37° C., the melanocyte cultures, in duplicate or triplicate, received one of the following: free complete melanocyte medium or DAG. Each melanocyte culture was then incubated for 6–7 days at 37° C.

Subsequently, each melanocyte culture was harvested, washed with 0.4 mM EDTA in PBS, treated with 1 ml of a mixture containing 0.13% trypsin and 0.2 mM EDTA, then incubated approximately 10 minutes at 37° C. followed by addition of 1 ml of PBS. A 0.5 ml aliquot of each resulting suspension was diluted to 10 ml total volume using isotonic saline and processed using a particle counter (Model ZM, Colter Science).

To determine melanin content, the remaining suspension was centrifuged for 5 minutes in a microcentrifuge. The supernatant was discarded and the resulting cell pellet dissolved in 0.1 ml of a 1M NaOH which was subsequently diluted with 0.4 ml of water. Melanin concentration was calculated by determination of optical density at 475 nanometers and values extrapolated by comparison with a standard curve of determinations for synthetic melanin, a measurement of melanogenesis which correlates extremely well with $^{14}$C-DOPA incorporation and with tyrosinase activity (Friedmann, P.S. and Gilchrest, B. A., *J. Cell. Physiol.* 133:88–94 (1987)). Melanin values were expressed as total melanin per culture, as melanin content per cell, or as percent of untreated controls.

In certain instances, phase contrast micrographs were taken using an inverted microscope after the cultures were washed once with phosphate buffered saline.

EXAMPLE 3

In-Vivo Experiments with Adult Guinea Pigs

Two adult guinea pigs were obtained from a strain known to have melanin in the epidermis, as well as in hair follicles. The guinea pigs were clipped and shaved to provide a large hairless area on the back. Two areas, 2 cm $\times$ 4 cm in size, with compatible baseline pigmentation, were chosen for the application of either (a) 50 ul of OAG (50 mg/ml) in dimethyl sulfoxide (DMSO) or (b) 50 ul of DMSO alone as a vehicle control. The animals were restrained for 10 minutes for each application to allow absorption of the test solutions before being returned to their cages. Applications were made daily for 7 days.

Increased pigmentation in the OAG-treated areas was observed and first apparent at 4–5 days and persisted for approximately one month, fading gradually afterwards. At all time points, the OAG-treated areas were darker in color than the vehicle-treated (DMSO) areas. The differences caused by OAG treatment and the increased pigmentation were visible to the unaided eye. These animals were observed and photographed to maintain a permanent record of the results, and the photographs are available upon request.

In addition, punch biopsies of OAG-treated, DMSO-treated and adjacent untreated skin were obtained 7 days after the last application (14 days after the first application). The biopsies were processed to yield 3 micron vertical cross-section specimens, and then stained with Fontana Mason, a stain which contains a reducing agent known to stain melanin a black color. A Perl's staining procedure, performed to exclude iron pigment as the source of color, was negative, thus further confirming that the stained material was melanin. In all specimens, the pigmentation is concentrated in the lower epidermis exactly as seen in normal skin at baseline and after tanning induced by sun exposure.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for increasing the melanin content of vertebrate melanocytes, comprising topically or subcutaneously administering to said vertebrate an effective amount of a diacylglycerol compound wherein the 3 position is a hydroxyl and the 1 and 2 positions are independently carboxylic acid esters 1 to 18 carbon atoms long in a pharmaceutically acceptable carrier.

2. The method of claim 1 wherein the diacylglycerol is 1-oleoyl-2-acetyl-glycerol.

3. A method for darkening skin in patients in need thereof comprising topically or subcutaneously administering to said patient an effective amount of a diacylglycerol compound, wherein the 3 position is a hydroxyl and the 1 and 2 positions are independently carboxylic acid esters 1 to 18 carbon atoms long, and a pharmaceutically acceptable carrier.

4. The method of claim 3 wherein the diacylglycerol is 1-oleoyl-2-acetyl-glycerol.

5. The method of claim 1 wherein the melanocytes are located in the skin.

6. The method of claim 1 wherein the melanocytes are located in the hair follicle.

* * * * *

UNITED STATES PATENT AND TRADEMARK OFFICE
CERTIFICATE OF CORRECTION

PATENT NO. : 5,352,440

DATED : October 4, 1994

INVENTOR(S) : Barbara A. Gilchrest and Philip R. Gordon

It is certified that error appears in the above-indentified patent and that said Letters Patent is hereby corrected as shown below:

On the Title Page, item [63], change "Ser. No. 635,405" to --Ser. No. 625,405--.

IN THE DRAWINGS:

Figure 1A, bottom figure legend, change "DIAGLYCEROL" to ---DIACYLGLYCEROL---.

Figure 1A, right figure legend, change "(-o-)" to ---(-●-)---.

Figure 1B:
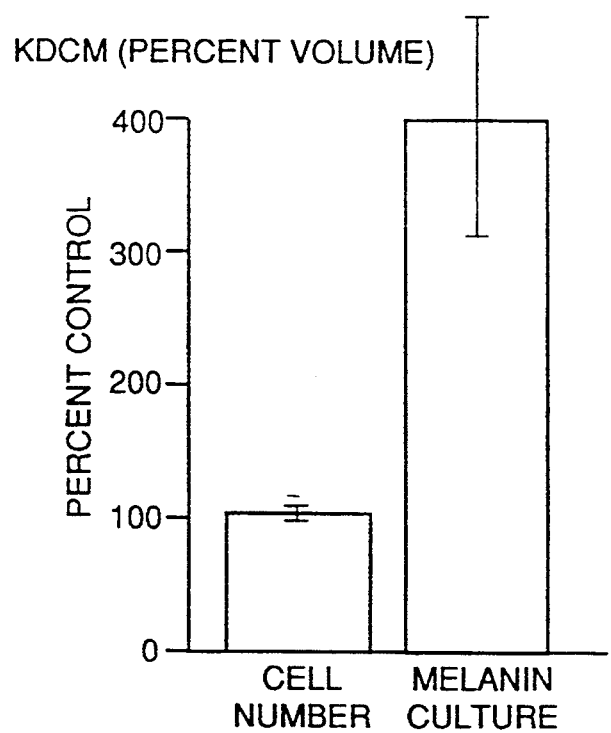

Figure 1B, top figure legend, change "KDCM (PERCENT VOLUME)" to ---DIACYLGLYCEROL---.

Signed and Sealed this

Twenty-eight Day of February, 1995

Attest:

BRUCE LEHMAN

Attesting Officer    Commissioner of Patents and Trademarks